(12) United States Patent
Famodu et al.

(10) Patent No.: US 7,009,089 B1
(45) Date of Patent: Mar. 7, 2006

(54) GENES ENCODING STEROL DELTA-14 REDUCTASE IN PLANTS

(75) Inventors: Omolayo O. Famodu, Newark, DE (US); Anthony J. Kinney, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 262 days.

(21) Appl. No.: 10/069,427

(22) PCT Filed: Sep. 27, 2000

(86) PCT No.: PCT/US00/26442

§ 371 (c)(1),
(2), (4) Date: Feb. 19, 2002

(87) PCT Pub. No.: WO01/23539

PCT Pub. Date: Apr. 5, 2001

Related U.S. Application Data

(60) Provisional application No. 60/156,820, filed on Sep. 30, 1999.

(51) Int. Cl.
*A01H 5/00* (2006.01)
*C12N 15/82* (2006.01)

(52) U.S. Cl. ..................... 800/298; 800/278; 435/419; 435/468

(58) Field of Classification Search ............... 536/23.2, 536/23.6; 435/468, 471, 320.1, 252.3, 419; 800/281, 298, 278
See application file for complete search history.

(56) References Cited

FOREIGN PATENT DOCUMENTS

| EP | 0644268 A2 | 7/1994 |
|---|---|---|
| WO | WO 97/48793 A1 | 12/1997 |
| WO | WO 98/45457 A1 | 10/1998 |

OTHER PUBLICATIONS

Margaret H. Lai et. al., Gene, vol. 140:41-49, 1994, The Identification of a Gene Family in the *Saccharomyces cerevisiae* Ergosterol Biosynthesis Pathway.

Leo W. Parks et. al., Lipids, vol. 30:227-230, 1995, Biochemical and Physiological Effects of Strerol Alterations in Yeast-A Review.

Lizette M. Palermo et. al., Curr. Genet., vol. 32:93-99, 1997, Assessment of the Essentiality of ERG Genes Late in Ergosterol Biosynthesis in *Saccharomyces cerevisiae*.

James H. Crowley et. al., Journal of Bacteriology, vol. 178:2991-2993, 1996, Aerobic Isolation of an ERG24 Null Mutant of *Saccharomyces cerevisiae*.

Christophe Marcireau et. al., Curr. Genet., vol. 22:267-272, Construction and Growth Properties of a Yeast Strain Defective in Sterol 14-Reductase.

Keith Barrett-Bee et. al., Acta. Biochim. Pol., vol. 42:465-479, 1995, Ergosterol Biosynthesis Inhibition: A Target for Antifungal Agents.

Warren Gish et. al., Nat. Genet., vol. 3:266-272, 1993, Identification of Protein Coding Regions by Database Similarity Search.

Stephen F. Altschul et. al., Nucleic Acids Research, vol. 25:3389-3402, 1997, Gapped Blast and PSI-Blast: A New Generation of Protein Database Search Programs.

Kathrin Schrick et. al., Genes & Development, vol. 14:1471-1484, 2000, Fackel is a Sterol C-14 Reductase Required for Organized Cell Division and Expansion in *Arabidopsis* Embryogenesis.

Jyan-Chyun Jang et. al., Genes Development, vol. 14:1485-1497, 2000, A Critical Role of Sterols in Embryonic Patterning and Meristem Programming Revealed by the Fackel Mutants of *Arabidopsis thaliana*.

Christopher C. Steel et al., Journal of Chromatography, 586 435-443, 1991, Radio-Detection High-Performance Liquid Chromatographic Enzyme Assay for Inhibitors of Fungal Sterol Delta-$^{14}$-Reductase.

*Primary Examiner*—Elizabeth F. McElwain
(74) *Attorney, Agent, or Firm*—Morgan & Finnegan, L.L.P.

(57) ABSTRACT

Disclosed are plant sterol biosynthetic enzymes, genes, and their uses.

12 Claims, 2 Drawing Sheets

Application No.: 10/069,427
7560*49 (BB1395USPCT)
Preliminary Amendment
Replacement Sheet Comparison of the Corn, Soybean (2), and Arabidopsis Sterol Delta-14 Reductases

```
p0097.cqrau67ra_fis.PRO      ----------------------------------------------------------
src3c.pk009.c1_fis.PRO       M------MESHVDLGFLLQALTPSWNSVPLLVG-------------------------
ssm.pk0031.d12_fis.PRO       M------MESHVDLGFLLQALTPSWNSVPLLVG-------------------------
8917585_(Arabidopsis).PRO    M-------------DLGVLLPSL----QSVYVLVF----------------------- p0097.cqrau67ra_fis.PRO      ---------------------------------------------PRVR---KNKVELSLLSGLANLC-
src3c.pk009.c1_fis.PRO       FFTYLAVAGSILPGKLVPGVALLDGTRLHYCCNGLLSLLLLVALLGIGA
ssm.pk0031.d12_fis.PRO       FFTYLAVAGSILPGKLVPGVALLDGTRLHYCCNGLLSLLLLVALLGIGA
8917585_(Arabidopsis).PRO    YFVYLAVAGEILPGKVIRGVLLSDGSQLRYRCNGLLALILLVAILGICA p0097.cqrau67ra_fis.PRO      KMGFVSPT-----AISDRGLELLSTTFAFSFLVTLILHFSGCKSQSKGSS--LKPH-LSG
src3c.pk009.c1_fis.PRO       KMGFVSPT-----AISDRGLELLSTTFAFSFLVTLILHFSGCKSQSKGSS--LKPH-LSG
ssm.pk0031.d12_fis.PRO       KLGIVSPL-----VVADRGLELLSATFIFCVLVTLALYVTGRSSSNKGSS--LKPH-VSG
8917585_(Arabidopsis).PRO p0097.cqrau67ra_fis.PRO      NLIHDWFGIQLNPQFMG-IDLKFFF-VRAGMGWLLINLSILMKSIQ-DGTLSQSMILY
src3c.pk009.c1_fis.PRO       NLIHDWFGIQLNPQFMG-IDLK-----AGMGWLLINLSILMKSIQ-DGTLSQSMILY
ssm.pk0031.d12_fis.PRO       NLVHDWFGIQLNPQFMS-IDLKFFF-VRAGMGWLLINLSILAKSVQ-DGSLSQSMILY
8917585_(Arabidopsis).PRO p0097.cqrau67ra_fis.PRO      QLFCALYILDYFVHEEYMTSTWDIIAERLGFMLVFGDLVWIPFSFSIQGWWLLMNSVELT
src3c.pk009.c1_fis.PRO       QLFCALYILDYFVHEEYMTSTWDIIAERLGFMLVFGDLVWIPFSFSIQGWWLLMNSVELT
ssm.pk0031.d12_fis.PRO       QIFCALYILDYFVHEEYMTSTWDIIAERLGFMLVFGDLLWIPFTFSIQGWWLLHNKVELT
8917585_(Arabidopsis).PRO p0097.cqrau67ra_fis.PRO      ------IFLIGYLVFRGANKQKHVFKKDPKAPIWGKPPKVV---GGKLLASGYWGIA
src3c.pk009.c1_fis.PRO       PAAIVANCFVFLIGYMVFRGANKQKHVFKKNPKAPIWGKPPKVI---GGKLLASGYWGIA
ssm.pk0031.d12_fis.PRO       PAAIVANCFVFLIGYMVFRGANKQKHVFKKNPKAPIWGKPPKVI---GGKLLASGYWGIA
8917585_(Arabidopsis).PRO    VPAIVVNCLVFLIGYMVFRGANKQHIFKKNPKTPIWGKPPVVV---GGKLLVSGYWGIA
```

FIG. 1A

```
p0097.cqrau67ra_fis.PRO        RHCNYLGDLLLALSFSLPCGVSSVVPYFYPTYLLILLVLRERRDEARCSQKYREIWAEYC
src3c.pk009.c1_fis.PRO         RHCNYLGDLMLALSFSLPCGISSPIPYFYPIYLLILLIWRERRDEARCAEKYREIWAEYR
ssm.pk0031.d12_fis.PRO         RHCNYLGDLMLALSFSLPCGISSPIPYFYPIYLLILLIWRERTDEARCAEKYREIWAEYR
8917585_(Arabidopsis).PRO      RHCNYLGDLMLALSFSLPCGISSPVPYFYPIYLLILLIWRERRDEVRCAEKYKEIWAEYL p0097.cqrau67ra_fis.PRO        KLVPWRILPYVY
src3c.pk009.c1_fis.PRO         KLVPWRILPYVY
ssm.pk0031.d12_fis.PRO         KLVPWRILPYVY
8917585_(Arabidopsis).PRO      RLVPWRILPYVY
```

FIG. 1B

SEQUENCE LISTING

<160> NUMBER OF SEQ ID NOS: 10

<210> SEQ ID NO 1
<211> LENGTH: 427
<212> TYPE: DNA
<213> ORGANISM: Glycine max
<220> FEATURE:
<221> NAME/KEY: unsure
<222> LOCATION: (360)
<223> OTHER INFORMATION: n=a,c,g or t

<400> SEQUENCE: 1

```
gtgatgatgg agtcacacgt ggatctaggt tttctccttc aagctctcac tccatcttgg      60
aactccgttc ctttgcttgt ggggttcttc acttacttgg ccgttgctgg atccattctc     120
cctggaaaac ttgttcctgg cgttgcacta ctcgatggaa ctcgtctaca ctattgctgc     180
aatggtctgc tctcgcttct tctgttggtt gcacttctcg ggatcggtgc caagatgggt     240
tttgtgtctc ccactgccat atcaaacaga ggacttgagc tgctgtccac aactttttgcc    300 ttcagttttc ttgtaaccct gatattgcat ttttccgggt gcaagtcaca aagtaaaggn    360
tcatcactaa agcctcatct cagtgggaac ctgatacacg attggtggtt tgggaataca    420
actaaaa                                                              427
```

<210> SEQ ID NO 2
<211> LENGTH: 126
<212> TYPE: PRT
<213> ORGANISM: Glycine max

<400> SEQUENCE: 2

```
Leu Gln Ala Leu Thr Pro Ser Trp Asn Ser Val Pro Leu Leu Val Gly
 1               5                  10                  15

Phe Phe Thr Tyr Leu Ala Val Ala Gly Ser Ile Leu Pro Gly Lys Leu
             20                  25                  30

Val Pro Gly Val Ala Leu Leu Asp Gly Thr Arg Leu His Tyr Cys Cys
         35                  40                  45

Asn Gly Leu Leu Ser Leu Leu Leu Val Ala Leu Leu Gly Ile Gly
     50                  55                  60

Ala Lys Met Gly Phe Val Ser Pro Thr Ala Ile Ser Asn Arg Gly Leu
```

```
                65                  70                  75                  80
Glu Leu Leu Ser Thr Thr Phe Ala Phe Ser Phe Leu Val Thr Leu Ile
                        85                  90                  95

Leu His Phe Ser Gly Cys Lys Ser Gln Ser Lys Gly Ser Ser Leu Lys
                100                 105                 110

Pro His Leu Ser Gly Asn Leu Ile His Asp Trp Trp Phe Gly
            115                 120                 125

<210> SEQ ID NO 3
<211> LENGTH: 667
<212> TYPE: DNA
<213> ORGANISM: Zea mays

<400> SEQUENCE: 3
ccacgcgtcc ggaagaacaa agtagagctg tccctttttgt ctggtctagc taacttatgc      60
atctttctta ttggctacct agtgttccga ggagctaaca agcaaaaaca tgtgttcaag     120
aaggacccca agctcctat atggggaaaa cctcccaaag ttgtcggggg aaagctacta      180
gcatctggtt actggggcat cgcaaggcac tgcaattatc tcggagacct gctgctagca     240
ctttcgttca gcttgccctg tggagtgagt tccgtggtcc atacttcta ccccacgtac      300
ctgctcattc tactggtctt gagggaaagg cgcgatgagg cgaggtgctc gcagaagtac     360
agggagatct gggcagagta ctgcaagctc gtgccgtgga ggatcctgcc ttatgtgtac     420
tgaagagacg gtagaaacca aggcagctca tggccctggg ccagctgtaa accttatttt     480
gtttgcccctt aaccagttgg tgaatgttga tgtagcactc ggtaaactgt gaccgtgcaa    540
acttttgtta ttgttggtcc atacatgttt ggaatcgtga atcagaccgc ctcacttggt     600
ggcaaaaaaa aaaaaaaaaa aaaaaaaaaa aaaaaaaaaa aaaaaaaaaa aaaaaaaaaa     660
aaaaaag                                                               667

<210> SEQ ID NO 4
<211> LENGTH: 140
<212> TYPE: PRT
<213> ORGANISM: Zea mays

<400> SEQUENCE: 4

Pro Arg Val Arg Lys Asn Lys Val Glu Leu Ser Leu Ser Gly Leu
 1               5                  10                  15

Ala Asn Leu Cys Ile Phe Leu Ile Gly Tyr Leu Val Phe Arg Gly Ala
                20                  25                  30

Asn Lys Gln Lys His Val Phe Lys Lys Asp Pro Lys Ala Pro Ile Trp
            35                  40                  45

Gly Lys Pro Pro Lys Val Gly Gly Lys Leu Ala Ser Gly Tyr
        50                  55                  60

Trp Gly Ile Ala Arg His Cys Asn Tyr Leu Gly Asp Leu Leu Leu Ala
65                  70                  75                  80

Leu Ser Phe Ser Leu Pro Cys Gly Val Ser Ser Val Val Pro Tyr Phe
                85                  90                  95

Tyr Pro Thr Tyr Leu Leu Ile Leu Leu Val Leu Arg Glu Arg Arg Asp
                100                 105                 110

Glu Ala Arg Cys Ser Gln Lys Tyr Arg Glu Ile Trp Ala Glu Tyr Cys
            115                 120                 125

Lys Leu Val Pro Trp Arg Ile Leu Pro Tyr Val Tyr
        130                 135                 140
```

<210> SEQ ID NO 5
<211> LENGTH: 1631
<212> TYPE: DNA
<213> ORGANISM: Glycine max

<400> SEQUENCE: 5

```
ccgcgttgga atttgcccat ctaaaacctc aatcttttac tgaaaagtct caactttgaa      60
ctcactcgaa gtgatgatgg agtcacacgt ggatctaggt tttctccttc aagctctcac     120
tccatcttgg aactccgttc ctttgcttgt ggggttcttc acttacttgg ccgttgctgg     180
atccattctc cctggaaaac ttgttcctgg cgttgcacta ctcgatggaa ctcgtctaca     240
ctattgctgc aatggtctgc tctcgcttct tctgttggtt gcacttctcg ggatcggtgc     300
caagatgggt tttgtgtctc ccactgccat atcagacaga ggacttgagc tgctgtccac     360
aactttgcc ttcagttttc ttgtaaccct gatattgcat ttttccggtt gcaagtcaca     420
aagtaaaggt tcatcactaa agcctcatct cagtggaaac ctgatacacg attggtggtt     480
tggtatacaa ctaaatccac agttcatggg tatcgacctc aaatttttct tgttagagc     540
tggaatgatg ggatggctac ttatcaattt atctattctt atgaagagca ttcaagatgg     600
tactttgagc cagtcaatga ttctctacca gctattctgt gcactataca tcctggacta     660
ttttgtacat gaagagtaca tgacatccac ctgggacata attgcagaga gactgggctt     720
catgttggtc tttggagatt tagtgtggat tccttttctct ttcagcatac agggatggtg     780
gctcttgatg aacagtgtgg agttaacacc agctgccatt gtagctaatt gctttgtgtt     840
cctgattgga tacatggtat ttcgaggagc aaacaagcaa aagcatgtgt tcaaaaagaa     900
tccaaaggct cctatctggg gtaagcctcc aaaagtcatt ggtggaaagc tacttgcttc     960
tggttattgg ggtattgcta gacactgtaa ttacctaggg gatttgatgc ttgctctctc    1020
ctttagctta ccatgtggga taagttcacc aattccatac ttctatccaa tttatcttct    1080
tattctgtta atctggagag agagaaggga tgaagctcgt tgcgccgaga gtatagaga    1140
gatatgggcc gagtatcgta aacttgttcc atggagaata ttgccttacg tttattagga    1200
tgaaaaaaa aagggcttca ccatgaattc ttcatcttgc cgatgttatt aagcacttcg    1260
atgtaaattg gttcttgttc ttgtggtttc aatcttggat cttttcttat tgagccatgt    1320
agctgcagga gagtgtttcg agggatttat cttaccatct atatttgtgt atcattatgc    1380
tgcagcctgc aggccttcat ttttcaatgg ccaactcttt ttgacttgtt ctatttgttt    1440
ttagatgaga atttcatggt caaagctcct aggcttaaaa aaacagtgtc atgttctatg    1500
ggaagtgcag gaagcaattc ggggactgca ggaagcaatt gcctttacat tgatatgctc    1560
aatggtactt taggcccttt aatgttcttg cttttcattt gtgagttatt attggcccca    1620
tttcatttgc a                                                        1631
```

<210> SEQ ID NO 6
<211> LENGTH: 374
<212> TYPE: PRT
<213> ORGANISM: Glycine max

<400> SEQUENCE: 6

```
Met Met Glu Ser His Val Asp Leu Gly Phe Leu Leu Gln Ala Leu Thr
 1               5                  10                  15

Pro Ser Trp Asn Ser Val Pro Leu Leu Val Gly Phe Phe Thr Tyr Leu
            20                  25                  30

Ala Val Ala Gly Ser Ile Leu Pro Gly Lys Leu Val Pro Gly Val Ala
        35                  40                  45
```

Leu Leu Asp Gly Thr Arg Leu His Tyr Cys Cys Asn Gly Leu Leu Ser
    50                  55                  60

Leu Leu Leu Leu Val Ala Leu Leu Gly Ile Gly Ala Lys Met Gly Phe
65                  70                  75                  80

Val Ser Pro Thr Ala Ile Ser Asp Arg Gly Leu Glu Leu Leu Ser Thr
                85                  90                  95

Thr Phe Ala Phe Ser Phe Leu Val Thr Leu Ile Leu His Phe Ser Gly
            100                 105                 110

Cys Lys Ser Gln Ser Lys Gly Ser Ser Leu Lys Pro His Leu Ser Gly
        115                 120                 125

Asn Leu Ile His Asp Trp Trp Phe Gly Ile Gln Leu Asn Pro Gln Phe
    130                 135                 140

Met Gly Ile Asp Leu Lys Phe Phe Val Arg Ala Gly Met Met Gly
145                 150                 155                 160

Trp Leu Leu Ile Asn Leu Ser Ile Leu Met Lys Ser Ile Gln Asp Gly
                165                 170                 175

Thr Leu Ser Gln Ser Met Ile Leu Tyr Gln Leu Phe Cys Ala Leu Tyr
            180                 185                 190

Ile Leu Asp Tyr Phe Val His Glu Glu Tyr Met Thr Ser Thr Trp Asp
        195                 200                 205

Ile Ile Ala Glu Arg Leu Gly Phe Met Leu Val Phe Gly Asp Leu Val
    210                 215                 220

Trp Ile Pro Phe Ser Phe Ser Ile Gln Gly Trp Trp Leu Leu Met Asn
225                 230                 235                 240

Ser Val Glu Leu Thr Pro Ala Ala Ile Val Ala Asn Cys Phe Val Phe
                245                 250                 255

Leu Ile Gly Tyr Met Val Phe Arg Gly Ala Asn Lys Gln Lys His Val
            260                 265                 270

Phe Lys Lys Asn Pro Lys Ala Pro Ile Trp Gly Lys Pro Pro Lys Val
        275                 280                 285

Ile Gly Gly Lys Leu Leu Ala Ser Gly Tyr Trp Gly Ile Ala Arg His
    290                 295                 300

Cys Asn Tyr Leu Gly Asp Leu Met Leu Ala Leu Ser Phe Ser Leu Pro
305                 310                 315                 320

Cys Gly Ile Ser Ser Pro Ile Pro Tyr Phe Tyr Pro Ile Tyr Leu Leu
                325                 330                 335

Ile Leu Leu Ile Trp Arg Glu Arg Arg Asp Glu Ala Arg Cys Ala Glu
            340                 345                 350

Lys Tyr Arg Glu Ile Trp Ala Glu Tyr Arg Lys Leu Val Pro Trp Arg
        355                 360                 365

Ile Leu Pro Tyr Val Tyr
    370

<210> SEQ ID NO 7
<211> LENGTH: 1364
<212> TYPE: DNA
<213> ORGANISM: Glycine max

<400> SEQUENCE: 7
ttcggcacga gtaaaacctc aatcttttac tgaaaagtct caactttgaa ctcactcgaa      60
gtgatgatgg agtcacacgt ggatctaggt tttctccttc aagctctcac tccatcttgg     120
aactccgttc ctttgcttgt ggggttcttc acttacttgg ccgttgctgg atccattctc     180
cctggaaaac ttgttcctgg cgttgcacta ctcgatggaa ctcgtctaca ctattgctgc     240

```
aatggtctgc tctcgcttct tctgttggtt gcacttctcg ggatcggtgc caagatgggt    300
tttgtgtctc ccactgccat atcagacaga ggacttgagc tgctgtccac aacttttgcc    360
ttcagttttc ttgtaaccct gatattgcat ttttccggtt gcaagtcaca agtaaaggt    420 tcatcactaa agcctcatct cagtggaaac ctgatacacg attggtggtt tggtatacaa    480
ctaaatccac agttcatggg tatcgacctc aaagctggaa tgatgggatg gctacttatc    540
aatttatcta ttcttatgaa gagcattcaa gatggtactt tgagccagtc aatgattctc    600
taccagctat tctgtgcact atacatcctg gactattttg tacatgaaga gtacatgaca    660
tccacctggg acataattgc agagagactg ggcttcatgt tggtctttgg agatttagtg    720
tggattcctt tctctttcag catacaggga tggtggctct tgatgaacag tgtggagtta    780
acaccagctg ccattgtagc taattgcttt gtgttcctga ttggatacat ggtatttcga    840
ggagcaaaca agcaaaagca tgtgttcaaa aagaatccaa aggctcctat ctggggtaag    900
cctccaaaag tcattggtgg aaagctactt gcttctggtt attggggtat tgctagacac    960
tgtaattacc tagggatttt gatgcttgct ctctcccttta gcttaccatg tgggataagt   1020
tcaccaattc catacttcta tccaatttat cttcttattc tgttaatctg gagagagaga   1080
acggatgaag ctcgttgcgc cgagaagtat agagagatat gggccgagta tcgtaaactt   1140
gttccatgga gaatattgcc ttacgtttat taggatgaaa aaaaaaaggg cttcaccatg   1200
aattcttcat cttgccgatg ttattaagca cttcgatgta aattggttct tgttcttgtg   1260
gtttcaatct tggatctttt cttattgagc catgtagctg caggagagtg tttcgaggga   1320
tttatcttac catctatatt tgtgtaaaaa aaaaaaaaaa aaaa                     1364
```

<210> SEQ ID NO 8
<211> LENGTH: 369
<212> TYPE: PRT
<213> ORGANISM: Glycine max

<400> SEQUENCE: 8

```
Met Met Glu Ser His Val Asp Leu Gly Phe Leu Leu Gln Ala Leu Thr
 1               5                  10                  15

Pro Ser Trp Asn Ser Val Pro Leu Leu Val Gly Phe Phe Thr Tyr Leu
             20                  25                  30

Ala Val Ala Gly Ser Ile Leu Pro Gly Lys Leu Val Pro Gly Val Ala
         35                  40                  45

Leu Leu Asp Gly Thr Arg Leu His Tyr Cys Cys Asn Gly Leu Leu Ser
     50                  55                  60

Leu Leu Leu Leu Val Ala Leu Leu Gly Ile Gly Ala Lys Met Gly Phe
 65                  70                  75                  80

Val Ser Pro Thr Ala Ile Ser Asp Arg Gly Leu Glu Leu Leu Ser Thr
                 85                  90                  95

Thr Phe Ala Phe Ser Phe Leu Val Thr Leu Ile Leu His Phe Ser Gly
            100                 105                 110

Cys Lys Ser Gln Ser Lys Gly Ser Ser Leu Lys Pro His Leu Ser Gly
        115                 120                 125

Asn Leu Ile His Asp Trp Trp Phe Gly Ile Gln Leu Asn Pro Gln Phe
    130                 135                 140

Met Gly Ile Asp Leu Lys Ala Gly Met Met Gly Trp Leu Leu Ile Asn
145                 150                 155                 160

Leu Ser Ile Leu Met Lys Ser Ile Gln Asp Gly Thr Leu Ser Gln Ser
                165                 170                 175
```

```
Met Ile Leu Tyr Gln Leu Phe Cys Ala Leu Tyr Ile Leu Asp Tyr Phe
            180                 185                 190

Val His Glu Glu Tyr Met Thr Ser Thr Trp Asp Ile Ile Ala Glu Arg
            195                 200                 205

Leu Gly Phe Met Leu Val Phe Gly Asp Leu Val Trp Ile Pro Phe Ser
            210                 215                 220

Phe Ser Ile Gln Gly Trp Trp Leu Leu Met Asn Ser Val Glu Leu Thr
225                 230                 235                 240

Pro Ala Ala Ile Val Ala Asn Cys Phe Val Phe Leu Ile Gly Tyr Met
                245                 250                 255

Val Phe Arg Gly Ala Asn Lys Gln Lys His Val Phe Lys Lys Asn Pro
            260                 265                 270

Lys Ala Pro Ile Trp Gly Lys Pro Lys Val Ile Gly Gly Lys Leu
            275                 280                 285

Leu Ala Ser Gly Tyr Trp Gly Ile Ala Arg His Cys Asn Tyr Leu Gly
            290                 295                 300

Asp Leu Met Leu Ala Leu Ser Phe Ser Leu Pro Cys Gly Ile Ser Ser
305                 310                 315                 320

Pro Ile Pro Tyr Phe Tyr Pro Ile Tyr Leu Leu Ile Leu Leu Ile Trp
                325                 330                 335

Arg Glu Arg Thr Asp Glu Ala Arg Cys Ala Glu Lys Tyr Arg Glu Ile
            340                 345                 350

Trp Ala Glu Tyr Arg Lys Leu Val Pro Trp Arg Ile Leu Pro Tyr Val
            355                 360                 365

Tyr
369

<210> SEQ ID NO 9
<211> LENGTH: 430
<212> TYPE: PRT
<213> ORGANISM: Ascobolus immersus

<400> SEQUENCE: 9

Met Gly Gly Lys Asp Tyr Glu Phe Gly Gly Pro Ile Gly Thr Gly Val
1               5                   10                  15

Leu Met Leu Ile Leu Pro Pro Ile Ser His Tyr Leu His Phe Leu Ile
            20                  25                  30

Thr Pro Arg Gly Ala Pro Pro Glu Phe Trp Ser Ala Pro Leu Glu
        35                  40                  45

Thr Leu Lys Ser Val Thr Pro Thr Phe Ser Ser Leu Phe Ser Leu His
    50                  55                  60

Ala Thr Leu Ala Val Ala Ala Tyr Tyr Leu Leu Leu Val Ala Leu Met
65                  70                  75                  80

Tyr Val Leu Pro Ala Glu Ile Ala Glu Gly Val Val Leu Lys Asp Gly
                85                  90                  95

Ser Arg Leu Lys Tyr Arg Cys Asn Ala Phe Thr Thr Phe Leu Val Phe
            100                 105                 110

Phe Thr Phe Leu Gly Thr Met Thr Val Leu Glu Gly Pro Thr Trp Trp
            115                 120                 125

Phe Trp Ser Tyr Leu Thr Asp Asn Phe Ala Gln Leu Gln Ser Ala Ser
            130                 135                 140

Ile Val Phe Ser Tyr Ala Met Ser Leu Trp Val Tyr Ile Arg Ser Tyr
145                 150                 155                 160

Arg Pro Met Pro Lys Gly Lys Glu Val Ile Leu Ser Pro Val Gly Phe
```

-continued

```
                165                 170                 175
Lys Gly Asn His Ile His Asp Phe Trp Met Gly Arg Glu Leu Asn Pro
            180                 185                 190
Arg Ile Gly Glu Trp Leu Asp Ile Lys Gln Leu His Glu Leu Arg Pro
        195                 200                 205
Gly Leu Met Gly Trp Ile Leu Phe Asn Leu Ala Trp Thr Val Lys Gln
    210                 215                 220
Tyr Asn Thr His Gly Phe Val Ser Asp Ser Ile Val Leu Val Asn Leu
225                 230                 235                 240
Phe Glu Thr Trp Tyr Val Val Asp Ala Leu Trp Asn Glu Ser Lys Val
                245                 250                 255
Leu Thr Thr Met Asp Ile Thr Thr Asp Gly Leu Gly Val Met Leu Leu
            260                 265                 270
Phe Gly Asn Ala Val Trp Val Pro Phe Met Tyr Cys Leu Gln Ala Arg
        275                 280                 285
Tyr Leu Ala Ser Phe Pro Val His Leu Gly Leu Gly Ile Ala Gly
    290                 295                 300
Val Leu Ala Val Gln Phe Thr Gly Tyr Ala Ile Phe Arg Gly Ala Asn
305                 310                 315                 320
Asn Gln Lys Asn Ala Phe Arg Thr Asn Pro Ala Asp Pro Ala Val Ser
                325                 330                 335
His Leu Lys Phe Met Thr Thr Lys Ser Gly Ser Lys Leu Leu Ile Ser
            340                 345                 350
Gly Trp Trp Gly Val Ala Arg His Val Asn Tyr Phe Gly Asp Trp Ile
        355                 360                 365
Met Ala Trp Ser Tyr Cys Leu Thr Thr Gly Phe Asn Thr Pro Leu Thr
    370                 375                 380
Tyr Phe Tyr Val Ile Tyr Phe Gly Ile Leu Leu His Arg Asp Arg
385                 390                 395                 400
Arg Asp Glu Ala Lys Cys Arg Glu Lys Tyr Gly Lys Asp Trp Asp Arg
                405                 410                 415
Tyr Cys Lys Val Val Lys Trp Arg Ile Ile Pro Gly Ile Tyr
            420                 425                 430

<210> SEQ ID NO 10
<211> LENGTH: 365
<212> TYPE: PRT
<213> ORGANISM: Arabidopsis thaliana

<400> SEQUENCE: 10

Met Asp Leu Gly Val Leu Leu Pro Ser Leu Gln Ser Val Tyr Val Leu
  1               5                  10                  15
Val Phe Tyr Phe Val Tyr Leu Ala Val Ala Gly Glu Ile Leu Pro Gly
                20                  25                  30
Lys Val Ile Arg Gly Val Leu Leu Ser Asp Gly Ser Gln Leu Arg Tyr
            35                  40                  45
Arg Cys Asn Gly Leu Leu Ala Leu Ile Leu Leu Val Ala Ile Leu Gly
        50                  55                  60
Ile Cys Ala Lys Leu Gly Ile Val Ser Pro Leu Val Val Ala Asp Arg
 65                  70                  75                  80
Gly Leu Glu Leu Leu Ser Ala Thr Phe Ile Phe Cys Val Leu Val Thr
                85                  90                  95
Leu Ala Leu Tyr Val Thr Gly Arg Ser Ser Ser Asn Lys Gly Ser Ser
            100                 105                 110
```

-continued

```
Leu Lys Pro His Val Ser Gly Asn Leu Val His Asp Trp Trp Phe Gly
        115                 120                 125
Ile Gln Leu Asn Pro Gln Phe Met Ser Ile Asp Leu Lys Phe Phe Phe
        130                 135                 140
Val Arg Ala Gly Met Met Gly Trp Leu Leu Ile Asn Leu Ser Ile Leu
145                 150                 155                 160
Ala Lys Ser Val Gln Asp Gly Ser Leu Ser Gln Ser Met Ile Leu Tyr
                165                 170                 175
Gln Ile Phe Cys Ala Leu Tyr Ile Leu Asp Tyr Phe Val His Glu Glu
                180                 185                 190
Tyr Met Thr Ser Thr Trp Asp Ile Ile Ala Glu Arg Leu Gly Phe Met
        195                 200                 205
Leu Val Phe Gly Asp Leu Leu Trp Ile Pro Phe Thr Phe Ser Ile Gln
        210                 215                 220
Gly Trp Trp Leu Leu His Asn Lys Val Glu Leu Thr Val Pro Ala Ile
225                 230                 235                 240
Val Val Asn Cys Leu Val Phe Leu Ile Gly Tyr Met Val Phe Arg Gly
                245                 250                 255
Ala Asn Lys Gln Lys His Ile Phe Lys Lys Asn Pro Lys Thr Pro Ile
                260                 265                 270
Trp Gly Lys Pro Pro Val Val Val Gly Gly Lys Leu Leu Val Ser Gly
        275                 280                 285
Tyr Trp Gly Ile Ala Arg His Cys Asn Tyr Leu Gly Asp Leu Met Leu
        290                 295                 300
Ala Leu Ser Phe Ser Leu Pro Cys Gly Ile Ser Ser Pro Val Pro Tyr
305                 310                 315                 320
Phe Tyr Pro Ile Tyr Leu Leu Ile Leu Leu Ile Trp Arg Glu Arg Arg
                325                 330                 335
Asp Glu Val Arg Cys Ala Glu Lys Tyr Lys Glu Ile Trp Ala Glu Tyr
                340                 345                 350
Leu Arg Leu Val Pro Trp Arg Ile Leu Pro Tyr Val Tyr
        355                 360                 365
```

GENES ENCODING STEROL DELTA-14 REDUCTASE IN PLANTS

This is a 371 of PCT/US00/26442, filed Sep. 27, 2000. This application claims the benefit of U.S. Provisional Application No. 60/156,820, filed Sep. 30, 1999.

FIELD OF THE INVENTION

This invention is in the field of plant molecular biology. More specifically, this invention pertains to nucleic acid fragments encoding sterol delta-14 reductase in plants and seeds.

BACKGROUND OF THE INVENTION

Sterols are cyclic hydrocarbon molecules that help regulate the fluidity of cellular membranes. Sterols are essential components in all eukaryotic cells, and inhibitors that completely block sterol synthesis will block cell division and generally lead to cell death. In humans the predominant membrane sterol is cholesterol, which serves its structural role in membranes, and also serves as the precursor to hormones, bile salts, and modified membrane components. In fungi, the predominant sterol is often ergosterol, which follows the same biosynthetic pathway as cholesterol but contains an additional methyl group and altered double-bond placements. In plants there are multiple sterols working in different combinations, with stigmosterol and sitosterol as the most common components. The plant sterols tend to have 29 carbons, versus the 28 carbons of ergosterol, and the 27 carbons of cholesterol, but all are synthesized from the common precursors squalene and lanosterol.

The biosynthetic pathway leading to the final sterol products is long and complicated, requiring significant amounts of cellular energy to drive the multiple NADH (and/or NADPH) driven reduction steps. One enzyme in this pathway, sterol delta-14 reductase has been extensively studied in fungi because of its involvement in ergosterol synthesis (Lai et al. (1994) *Gene* 140: 4149; Parks et al. (1995) *Lipids* 30: 227–230). Mutants in sterol delta-14 reductase accumulate the aberrant sterol ignosterol, and can be supplemented with nutrients and growth conditions to survive (Palermo et al. (1997) *Curr Genet* 32: 93–99; Crowley et al. (1996) *J Bacteriol* 178: 2991–2993). The gene encoding this enzyme has been cloned and studied as a target for fungicidal agents (Marcireau et al. (1992) *Curr Genet* 22: 267–272; Barrett-Bee and Dixon (1995) *Acta Biochim Pol* 42: 465–479).

Prior to the instant invention, no plant sterol delta-14 reductase genes have been isolated. Availability of such plant genes will enable one to alter sterol production and/or composition in plants, to identify compounds that may be used as novel herbicides and fungicides, and to identify mutants of these genes that are resistant to these herbicides that will enable the production of herbicide-resistant crops.

SUMMARY OF THE INVENTION

The present invention is directed to an isolated polynucleotide comprising a nucleotide sequence selected from the group consisting of: (a) a first nucleotide sequence encoding a polypeptide of at least 126 amino acids having at least 50% identity based on the Clustal method of alignment when compared to a polypeptide consisting of SEQ ID NO:2, or preferably 369 amino acids having at least 82% identity based on the Clustal method of alignment when compared to a polypeptide selected from the group consisting of SEQ ID NOs:4, 6, and 8, or (b) a second nucleotide sequence comprising the complement of the first nucleotide sequence.

In a second embodiment, it is preferred that the isolated polynucleotide of the claimed invention comprises a first nucleotide sequence which comprises a nucleic acid sequence selected from the group consisting of SEQ ID NOs:1, 3, 5, and 7 that codes for the polypeptide selected from the group consisting of SEQ ID NOs:2, 4, 6, and 8.

In a third embodiment, this invention concerns an isolated polynucleotide comprising a nucleotide sequence of at least one of 300 (preferably at least one of 200, most preferably at least one of 125) contiguous nucleotides derived from a nucleotide sequence selected from the group consisting of SEQ ID NOs:1, 3, 5, and 7 and the complement of such nucleotide sequences.

In a fourth embodiment, this invention relates to a chimeric gene comprising an isolated polynucleotide of the present invention operably linked to at least one suitable regulatory sequence.

In a fifth embodiment, the present invention concerns an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

In a sixth embodiment, the invention also relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

In a seventh embodiment, the invention concerns a plant sterol delta-14 reductase polypeptide of at least 126 amino acids comprising at least 50% identity based on the Clustal method of alignment when compared to a polypeptide consisting of SEQ ID NO:2, or preferably 369 amino acids comprising at least 82% identity based on the Clustal method of alignment when compared to a polypeptide selected from the group consisting of SEQ ID NOs:4, 6, and 8,.

In an eighth embodiment, the invention relates to a method of selecting an isolated polynucleotide that affects the level of expression of a plant sterol delta-14 reductase polypeptide or enzyme activity in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level of the plant sterol delta-14 reductase polypeptide or enzyme activity in the host cell containing the isolated polynucleotide; and (d) comparing the level of the plant sterol delta-14 reductase polypeptide or enzyme activity in the host cell containing the isolated polynucleotide with the level of the plant sterol delta-14 reductase polypeptide or enzyme activity in the host cell that does not contain the isolated polynucleotide.

In a ninth embodiment, the invention concerns a method of obtaining a nucleic acid fragment encoding a substantial portion of a plant sterol delta-14 reductase polypeptide, preferably a plant plant sterol delta-14 reductase polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, and 7, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a plant sterol delta-14 reductase amino acid sequence.

In a tenth embodiment, this invention relates to a method of obtaining a nucleic acid fragment encoding all or a substantial portion of the amino acid sequence encoding a plant sterol delta-14 reductase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In an eleventh embodiment, this invention concerns a composition, such as a hybridization mixture, comprising an isolated polynucleotide of the present invention.

In a twelfth embodiment, this invention concerns a method for positive selection of a transformed cell comprising: (a) transforming a host cell with the chimeric gene of the present invention or an expression cassette of the present invention; and (b) growing the transformed host cell, preferably a plant cell, such as a monocot or a dicot, under conditions which allow expression of the plant sterol delta-14 reductase polynucleotide in an amount sufficient to complement a null mutant to provide a positive selection means.

In a thirteenth embodiment, this invention relates to a method of altering the level of expression of a sterol delta-14 reductase in a host cell comprising: (a) transforming a host cell with a chimeric gene of the present invention; and (b) growing the transformed host cell under conditions that are suitable for expression of the chimeric gene wherein expression of the chimeric gene results in production of altered levels of the sterol delta-14 reductase in the transformed host cell.

A further embodiment of the instant invention is a method for evaluating at least one compound for its ability to inhibit the activity of a sterol delta-14 reductase, the method comprising the steps of: (a) transforming a host cell with a chimeric gene comprising a nucleic acid fragment encoding a sterol delta-14 reductase polypeptide, operably linked to suitable regulatory sequences; (b) growing the transformed host cell under conditions that are suitable for expression of the chimeric gene wherein expression of the chimeric gene results in altered production, and/or ratios, of phytosterols in the transformed host cell; (c) optionally purifying the sterol delta-14 reductase polypeptide expressed by the transformed host cell; (d) treating the sterol delta-14 reductase polypeptide with a compound to be tested; and (e) comparing the activity of the sterol delta-14 reductase polypeptide that has been treated with a test compound to the activity of an untreated sterol delta-14 reductase polypeptide, thereby selecting compounds with potential for inhibitory activity.

BRIEF DESCRIPTION OF THE DRAWINGS AND SEQUENCE LISTINGS

The invention can be more fully understood from the following detailed description and the accompanying drawings and Sequence Listing which form a part of this application.

FIGS. 1A and 1B shows a comparison of the amino acid sequences encoded by a corn and two soybean sterol delta-14 reductase cDNAs (SEQ ID NOs:4, 6, and 8, respectively), and the *Arabidopsis thaliana* sequence (SEQ ID NO:10) that is the closest BLAST homolog.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Sterol Delta-14 Reductase

| | | SEQ ID NO: | |
| --- | --- | --- | --- |
| Protein | Clone Designation | (Nucleotide) | (Amino Acid) |
| Soybean sterol delta-14 reductase | src3c.pk009.c1 | 1 | 2 |
| Corn sterol delta-14 reductase | p0097.cqrau67ra:fis | 3 | 4 |
| Soybean sterol delta-14 reductase | src3c.pk009.c1:fis | 5 | 6 |
| Soybean sterol delta-14 reductase | ssm.pk0031.d12:fis | 7 | 8 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 300 contiguous nucleotides, preferably 200 contiguous nucleotides, more preferably 125 nucleotides, again more preferably 60 contiguous nucleotides, once again more preferably at least one of 40 contiguous nucleotides, and most preferably one of at least 30 contiguous nucleotides derived from SEQ ID NOs:1, 3, 5, and 7, or the complement of such sequences.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, and 7, and the complement of such nucleotide sequences may be used in methods of selecting an isolated polynucleotide that affects the expression of a plant sterol delta-14 reductase polypeptide in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA—DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6× SSC, 0.5% SDS at room temperature for 15 min, then repeated with 2× SSC, 0.5% SDS at 45° C. for 30 min, and then repeated twice with 0.2× SSC, 0.5% SDS at 50° C. for 30 min. A more preferred set of stringent conditions uses higher temperatures in which the washes are identical to those above except for the temperature of the final two 30 min washes in 0.2× SSC, 0.5% SDS was increased to 60° C. Another preferred set of highly stringent conditions uses two final washes in 0.1× SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' non-coding sequences" refer to nucleotide sequences located downstream of a coding, sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Null mutant" refers here to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence selected from the group consisting of: (a) first nucleotide sequence encoding a polypeptide of at least 126 amino acids having at least 50% identity based on the Clustal method of alignment when compared to a polypeptide consisting of SEQ ID NO:2, or preferably 369 amino acids having at least 82% identity based on the Clustal method of alignment when compared to a polypeptide selected from the group consisting of SEQ ID NOs:4, 6, and 8, or (b) a second nucleotide sequence comprising the complement of the first nucleotide sequence.

Preferably, the first nucleotide sequence comprises a nucleic acid sequence selected from the group consisting of SEQ ID NOs:1, 3, 5, and 7, that codes for the polypeptide selected from the group consisting of SEQ ID NOs:2, 4, 6, and 8.

Nucleic acid fragments encoding at least a portion of several sterol delta-14 reductase have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other plant sterol delta-14 reductase, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate fill length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 300 (preferably one of at least 200, most preferably one of at least 125) contiguous nucleotides derived from a nucleotide sequence selected from the group consisting of SEQ ID NOs:1, 3, 5, and 7 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a plant sterol delta-14 reductase polypeptide, preferably a substantial portion of a plant plant sterol delta-14 reductase polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, and 7, and the complement of such nucleotide sequences; and amplifying a nucleic acid fragment (preferably a cDNA inserted in a cloning vector) using the oligonucleotide primer. The amplified nucleic acid fragment preferably will encode a portion of a plant sterol delta-14 reductase polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of phytosterols in those cells.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a polypeptide of at least 126 amino acids having at least 50% identity based on the Clustal method of alignment when compared to a polypeptide consisting of SEQ ID NO:2, or preferably 369 amino acids having at least 82% identity based on the Clustal method of alignment when compared to a polypeptide selected from the group consisting of SEQ ID NOs:4, 6, and 8.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded sterol delta-14 reductase. An example of a vector for high level expression of the instant polypeptides in a bacterial host is provided (Example 6).

Additionally, the instant polypeptides can be used as a target to facilitate design and/or identification of inhibitors of those enzymes that may be useful as herbicides. This is desirable because the polypeptides described herein catalyzes an important step in phytosterol biosynthesis. Accordingly, inhibition of the activity of one or more of the enzymes described herein could lead to inhibition of plant growth. Thus, the instant polypeptides could be appropriate for new herbicide discovery and design.

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries: Isolation and Sequencing of cDNA Clones cDNA libraries representing mRNAs from various corn and soybean tissues were prepared. The characteristics of the libraries are described below.

TABLE 2 cDNA Libraries from Corn and Soybean

| Library | Tissue | Clone |
|---|---|---|
| p0097 | V9 7 cm whorl section + ECB1, screened 1 B73 + ECB1:7-cm whorl section Growth conditions: field plots; these plants have been infested with ECB four times prior to harvest. Growth stage: unknown; V9 or V10 | p0097.cqrau67ra:fis |
| src3c | Soybean 8 day old root infected with cyst nematode | src3c.pk009.c1 |
| ssm | Soybean Shoot Meristem | ssm.pk0031.d12:fis | cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765–3772). The in vitro transposition system places unique binding sites randomly throughout a population of large DNA molecules. The transposed DNA is then used to transform DH 10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

Example 2

Identification of cDNA Clones cDNA clones encoding sterol delta-14 reductase were identified by conducting BLAST (Basic Local Alignment Search Tool; Altschul et al. (1993) *J. Mol. Biol.* 215: 403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389–3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Sterol Delta-14 Reductase

The BLASTX search using the EST sequences from clones listed in Table 3 revealed similarity of the polypeptides encoded by the cDNAs to soybean sterol delta-14 reductase from *Ascobolus immersus* (Genbank Accession No. 1805625). Shown in Table 3 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 3

BLAST Results for Sequences Encoding Polypeptides Homologous to Soybean Sterol Delta-14 Reductase

| Clone | Status | BLAST pLog Score [gi 1805625] |
|---|---|---|
| src3c.pk009.c1 | EST | 6.70 |

The sequence of the entire cDNA insert in the clones listed in Table 3 was determined. Further sequencing and searching of the DuPont proprietary database allowed the identification of other corn and soybean clones encoding sterol delta-14 reductase. The BLASTX search using the EST sequences from clones listed in Table 4 revealed similarity of the polypeptides encoded by the cDNAs to sterol delta-14 reductases from *Arabidopsis thaliana* (NCBI General Identifier Nos. gi 8917585 and gi 8980704). Shown in Table 4 are the BLAST results for individual ESTs ("EST"), the sequences of the entire cDNA inserts comprising the indicated cDNA clones ("FIS"), sequences of contigs assembled from two or more ESTs ("Contig"), sequences of contigs assembled from an FIS and one or more ESTs ("Contig*"), or sequences encoding the entire protein derived from an FIS, a contig, or an FIS and PCR ("CGS"):

TABLE 4

BLAST Results for Sequences Encoding Polypeptides Homologous to *Arabidopsis* Sterol Delta-14 Reductases

| Clone | Status | BLAST pLog Score gi 8917585 |
|---|---|---|
| p0097.cqrau67ra:fis | FIS | 62.70 |
| src3c.pk009.c1:fis | FIS | >180.00 |
| ssm.pk0031.d12:fis | FIS | 174.00 |

FIGS. 1A and 1B presents an alignment of the amino acid sequences set forth in SEQ ID NOs:4, 6, and 8, and the *Arabidopsis thaliana* sequence (SEQ ID NO:10). The data in Table 5 represents a calculation of the percent identity of the amino acid sequences set forth in SEQ ID NOs:2, 4, 6, and 8, and the *Ascobolus immersus* and the *Arabidopsis thaliana* sequences (SEQ ID NOs:9 and 10). The nucleotide and polypeptide sequences contained in SEQ ID NOs:1 and 2, respectively, were part of the provisional filing of this application (U.S. Provisional Application No. 60/156,820, filed Sep. 30, 1999). The closest art at the time of the provisional filing was the *Ascobolus immersus* enzyme. The *Arabidopsis* Genbank submission is dated Jul. 5, 2000. The percent identity of SEQ ID NO:2 to the *Arabidopsis thaliana* sequence (SEQ ID NO:10, Jang et al. (2000) *Genes Dev.* 14:1485–1497) is 64.3%.

TABLE 5

Percent Identity of Amino Acid Sequences Deduced From the Nucleotide Sequences of cDNA Clones Encoding Polypeptides Homologous to Sterol Delta-14 Reductases

| | Percent Identity to | |
|---|---|---|
| SEQ ID NO. | gi 1805625 | gi 8917585 |
| 2 | 21.4% | |
| 4 | | 76.4% |
| 6 | | 81.1% |
| 8 | | 78.6% |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY≈10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a sterol delta-14 reductase. These sequences represent the first plant (SEQ ID NO:2) and first corn and soybean sequences encoding sterol delta-14 reductase known to Applicant.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) Sci. Sin. Peking 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the $^{35}$S promoter from Cauliflower Mosaic Virus (Odell et al. (1985) Nature 313:810–812) and the 3' region of the nopaline synthase gene from the T-DNA of the Ti plasmid of Agrobacterium tumefaciens.

The particle bombardment method (Klein et al. (1987) Nature 327:70–73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833–839).

Example 5

Expression of Chimeric Genes in Dicot Cells

A seed-specific expression cassette composed of the promoter and transcription terminator from the gene encoding the β subunit of the seed storage protein phaseolin from the bean Phaseolus vulgaris (Doyle et al. (1986) J. Biol. Chem. 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba 1. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the $^{35}$S promoter from Cauliflower Mosaic Virus (Odell et al.

(1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/ml hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 μg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 μL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 7

Evaluating Compounds for Their Ability to Inhibit the Activity of Sterol Delta-14 Reductase The polypeptides described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for sterol delta-14 reductase are presented by Steel (1991) *J Chromatogr* 31:435–43.

The invention claimed is:

1. An isolated polynucleotide comprising:
   (a) a nucleotide sequence encoding a sterol delta-14 reductase polypeptide, wherein the polypeptide has an amino acid sequence of at least 85% sequence identity, based on the Clustal method of alignment wherein the default parameters for multiple alignment are GAP PENALTY=10, GAP LENGTH PENALTY=10 and default parameters for pairwise alignments are KTUPLE 1, GAP PENALTY=3, WINDOW=5 and DIAGONALS SAVED=5, when compared to one of SEQ ID NO: 6 or 8, or
   (b) a complement of the nucleotide sequence, wherein the complement and the nucleotide sequence consist of the same number of nucleotides and are 100% complementary.

2. The polynucleotide of claim 1, wherein the amino acid sequence of the polypeptide has at least 90% sequence identity, based on the Clustal method of alignment wherein the default parameters for multiple alignment are GAP PENALTY=10, GAP LENGTH PENALTY=10 and default parameters for pairwise alignments are KTUPLE 1, GAP PENALTY=3, WINDOW=5 and DIAGONALS SAVED=5, when compared to one of SEQ ID NO:6 or 8.

3. The polynucleotide of claim 1, wherein the amino acid sequence of the polypeptide has at least 95% sequence identity, based on the Clustal method of alignment wherein the default parameters for multiple alignment are GAP PENALTY=10, GAP LENGTH PENALTY=10 and default parameters for pairwise alignments are KTUPLE 1, GAP PENALTY=3, WINDOW=5 and DIAGONALS SAVED=5, when compared to one of SEQ ID NO:6 or 8.

4. The polynucleotide of claim 1, wherein the amino acid sequence of the polypeptide comprises one of SEQ ID NO:6 or 8.

5. The polynucleotide of claim 1 wherein the nucleotide sequence comprises one of SEQ ID NO: 5 or 7.

6. A vector comprising the polynucleotide of claim 1.

7. A recombinant DNA construct comprising the polynucleotide of claim 1 operably linked to at least one regulatory sequence.

8. A method for transforming a cell, comprising transforming a cell with the polynucleotide of claim 1.

9. A cell comprising the recombinant DNA construct of claim 7.

10. A method for producing a plant comprising transforming a plant cell with the polynucleotide of claim 1 and regenerating a plant from the transformed plant cell.

11. A plant comprising the recombinant DNA construct of claim 7.

12. A seed comprising the recombinant DNA construct of claim 7.

* * * * *